United States Patent
Wanna

(10) Patent No.: US 8,700,182 B2
(45) Date of Patent: *Apr. 15, 2014

(54) MEDICAL PACING WIRES

(71) Applicant: Fady S. Wanna, Macon, GA (US)

(72) Inventor: Fady S. Wanna, Macon, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/662,949

(22) Filed: Oct. 29, 2012

(65) Prior Publication Data

US 2013/0053937 A1 Feb. 28, 2013

Related U.S. Application Data

(63) Continuation-in-part of application No. 13/417,066, filed on Mar. 9, 2012, now Pat. No. 8,532,791.

(60) Provisional application No. 61/451,104, filed on Mar. 9, 2011.

(51) Int. Cl.
 *A61N 1/00* (2006.01)

(52) U.S. Cl.
 USPC .......................................... 607/126

(58) Field of Classification Search
 USPC .............. 607/126, 116, 119, 149; 606/33, 41, 606/139, 198
 See application file for complete search history.

(56) References Cited

U.S. PATENT DOCUMENTS

| 5,171,252 A | 12/1992 | Friedland |
| 5,350,419 A | 9/1994 | Bendel et al. |
| 6,746,461 B2 | 6/2004 | Fry |
| 2008/0077174 A1* | 3/2008 | Mische .......................... 606/198 |
| 2010/0137928 A1 | 6/2010 | Duncan et al. |

FOREIGN PATENT DOCUMENTS

WO WO2006064490 6/2006

* cited by examiner

*Primary Examiner* — Robert N Wieland
(74) *Attorney, Agent, or Firm* — Brient Globerman, LLC

(57) ABSTRACT

A medical pacing wire comprising a clamp that is adapted to be moved between an open position and a closed position and further adapted to allow a user to attach an electrode to a living tissue. In particular embodiments, the medical pacing wire may include a memory shape alloy having a memory state, which is adapted to cause the clamp to move from the closed position toward the open position when the memory shape alloy is caused to move from a non-memory state to the memory state. Also, in some embodiments, the clamp may comprise a superelastic material, and the medical pacing wire may be adapted to allow a user to remotely cause the clamp to substantially release the living tissue that has been closed within the clamp without substantially damaging the living tissue.

8 Claims, 12 Drawing Sheets

MEDICAL PACING WIRES

CROSS REFERENCE TO RELATED APPLICATION

This application is a continuation-in-part of U.S. Non-Provisional application Ser. No. 13/417,066, which was filed on Mar. 9, 2012, entitled "Medical Pacing Wires", which claims the benefit of U.S. Provisional Application No. 61/451,104, entitled "Medical Pacing Wires", filed Mar. 9, 2011, both of which are hereby incorporated herein in their entirety.

BACKGROUND

Cardiac surgical procedures have become very common worldwide. By some estimates, 700,000 are performed annually in the USA. Despite their complexities, the risk associated with these procedures has steadily declined over the years. However, the temporary pacing wires that are placed on essentially every heart at the completion of the procedure have not improved their safety profile in close to two decades. As a matter of fact, surgeons continue to use temporary pacing wires that were designed in 1992. These temporary pacing wires/leads, when removed several days post-operatively, continue to pose a significant risk of bleeding to the patient. Such bleeding could lead, in about 1% of cases, to tamponade and even death. These devices are so hazardous that some surgeons prefer to refrain from using them rather than expose the patient to the bleeding risks.

Several different prior art pacing wires will now be discussed for background purposes. In various prior art pacing wires, a distal end of the pacing wire is secured to the heart with a suture. A few days later, the pacing wire is removed by pulling on the proximal end of the wire, which is outside the patient's chest, in essence tearing the tissue attached to the distal end and pulling it through the chest wall. The major complication of such a system is the potential bleeding complications that may ensue by ripping a portion of the heart tissue in order to dislodge the sutured distal end of the device. Another minor, yet annoying, feature of this prior art pacing wire is encountered if the surgeon decides to lift the heart and inspect it after securing the pacing wire in place. In such cases, he or she will often dislodge/rip the distal end of the pacing wire off of the patient's heart, and must then reattach the device to the heart. This may lead to intraoperative bleeding that can make the surgery more difficult to complete. Another shortcoming of this device is that, when securing the distal electrode to the heart with a suture, bleeding may occur from the suture itself as the suture passes into the heart tissue. In such cases, additional sutures may be required to stop the bleeding.

In other prior art pacing wires, the pacing wire's distal pacing electrode is driven into, rather than sutured to, the heart tissue. In such pacing wires, the distal electrode is attached to a helical suture that has a curved needle at one end. The curved needle is driven into the heart and pulled through until the distal electrode is embedded within the heart tissue. The curved needle and a portion of the helical suture are then cut leaving the distal electrode positioned inside the heart tissue. A few days later, the pacing wire is removed, by pulling on the proximal end of the wire/lead that is outside the patient's chest. In this case, instead of tearing the tissue that is attached to the distal end of the pacing wire, and pulling the distal electrode through the chest wall, the distal electrode slips out of the myocardium/tissue of the heart and is removed. Unfortunately, however, bleeding can still occur from the tract evacuated by the electrode and attached wire with all of the associated morbid consequences including death. Furthermore, this arrangement is also subject to all of the other shortcomings that plague the prior art arrangement discussed above in terms of dislodgement and bleeding associated with resecuring the electrode to the heart.

Yet another prior art pacing wire arrangement calls for securing a permanent clip to the heart that has an antenna (in the form of two parallel rabbit ears), or a round receptacle through which a pacing wire may be introduced. The problems with this design are multifold. First, since the electrode and pacing wire are loosely attached together, the potential for the wire to dislodge from the electrode antenna in such a way as to stop pacing is very high as a result of: (1) the beating of the patient's heart; (2) the patient's movements; or (3) the patient's respiratory fluctuations. Also, the permanent electrode is disadvantageously left on the heart permanently. In addition, securing the electrode to the heart poses the risk of causing bleeding as described above in regard to the arrangements of FIGS. 1 and 2. Lastly, disengaging the wire from the permanent electrode could potentially be hazardous.

In brief, currently known cardiac pacing wires continue to present significant hazards to patients. Accordingly, there is a need for improved, safer cardiac pacing wires.

SUMMARY

A medical pacing wire according to various embodiments comprises: (1) an elongated flexible conductor (e.g., an insulated wire with two stripped ends that serve as electrodes, or any other suitable conductor); (2) a clamp attached to the flexible conductor's distal end; and (3) a needle (e.g., a Keith needle) that is attached to the flexible conductor's proximal end. In particular embodiments, the Keith needle is scored for easy removal.

In various embodiments, the clamp includes first and second opposing clamp members and a grip portion that may be used to move the clamp between: (1) an open position in which the first and second clamp members are spaced a first distance apart from each other; and (2) a closed position in which the first and second clamp members are spaced a second distance apart from each other, the second distance being shorter than the first distance. The medical pacing wire may be adapted to allow a user to attach an electrode to a living tissue by: (1) moving the clamp into the open position; (2) positioning the clamp so that the living tissue is positioned between the clamp's first and second opposing clamp portions; (3) closing the clamp until the first and second clamp portions are in the closed position and exert opposing compressive forces on opposite sides of the living tissue and thereby maintain the electrode in engagement with the living tissue.

In various embodiments, the clamp is adapted to allow a user to remotely cause the clamp to at least substantially release the living tissue without substantially damaging the tissue. For example, the clamp may be made of a material, such as a metal shape alloy, that is configured to change its shape in response to being exposed to a particular change in temperature or to an electric current. As one example, the clamp is made of a memory shape alloy, such as Nitinol, that is adapted: (1) to remain in the shape of a clamp at standard animal body temperatures; and (2) to relax into the form of a flexible wire in response to being cooled to a temperature that is a few degrees below standard animal body temperatures. This may allow a user to remotely release the clamp from the living tissue (e.g., without substantially damaging the living tissue) by simply subjecting the proximal end of the pacing wire to an appropriate change in temperature. The user may then withdraw the distal end of the pacing wire from the individual's body in the form of a low-profile, flexible wire rather than in the form of a clamp.

In a particular embodiment, the pacing wire may include a clamp and an actuator, the actuator being adapted to respond to a change in temperature to bias the clamp towards an open position from a closed position. In another embodiment, the pacing wire may include a physical mechanism (similar to a bike brake cable) that is adapted to allow a user to remotely open and close the clamp from outside a patient's body while the clamp is attached to tissue inside the patient's body.

To use the pacing wire to pace a user's heart, a user (typically a cardiac surgeon): (1) passes the Keith needle and the proximal end of the pacing wire through the patient's chest wall and skin; (2) attaches the clamp to a portion of the patient's heart; (3) snaps the Keith needle off at a score line on the Keith needle; and (4) connects the proximal end of the pacing wire to a pacemaker. The pacemaker is then used to pace the patient's heart by sending periodic electrical pulses to the heart through the pacing wire.

Once a physician determines that the patient's heart no longer requires pacing, a user may remove the pacing wire by detaching the clamp from the patient's heart, and then removing the clamp through the patient's chest wall. In the case of a pacing wire that has a clamp made from a memory shape alloy, this may be done, for example, by subjecting the proximal end of the pacing wire to a change in temperature (e.g., by submerging the proximal end of the pacing wire in liquid nitrogen). In this example, due to the wire's thermal conductivity, the clamp's temperature will soon decrease, which will, in turn, cause the wire forming the clamp to relax from its clamp shape into the shape of a flexible wire. In another example, the change in temperature may be affected by subjecting the pacing wire to a voltage, which may cause the clamp's temperature to increase, which will in turn, cause the wire forming the clamp to relax from its clamp shape. A user may then remove the wire from the patient's body through the patient's chest wall.

In other embodiments, the clamp may be made from a superelastic material and the pacing wire may further comprise an actuator in mechanical contact with the clamp. In such embodiments, the actuator may be made of a memory shape alloy adapted to change its shape in response to a change in temperature. In various embodiments, the change in shape may cause the actuator to bias the clamp to an open position, allowing a user to remove the clamp from a piece of tissue to which it was clamped.

In the various embodiments in which a more traditional mechanical clamp is used (which is configured to be remotely opened and closed via suitable mechanical or electromechanical means), the operator simply: (1) uses the mechanical or electromechanical control mechanism to release the clamp from the patient's heart; and (2) withdraws the wire (including the clamp) through the patient's chest wall. For example, in a particular embodiment in which a bike brake cable is used to remotely control the opening/closing of the clamp, the user may: (1) open the clamp by pushing on the end of the brake cable; and then (2) withdraw the wire and the clamp from the patient's body through the patient's chest wall.

BRIEF DESCRIPTION OF THE DRAWINGS

Figure 1:
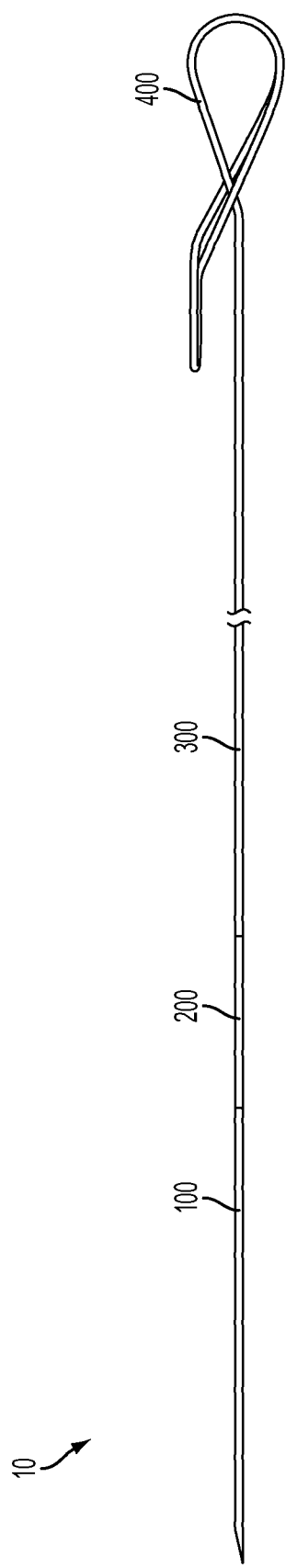

Having thus described various embodiments in general terms, reference will now be made to the accompanying drawings, which are not necessarily drawn to scale, and wherein:

FIG. 1 is a schematic diagram of a cardiac pacing wire according to a particular embodiment.

Figure 2:
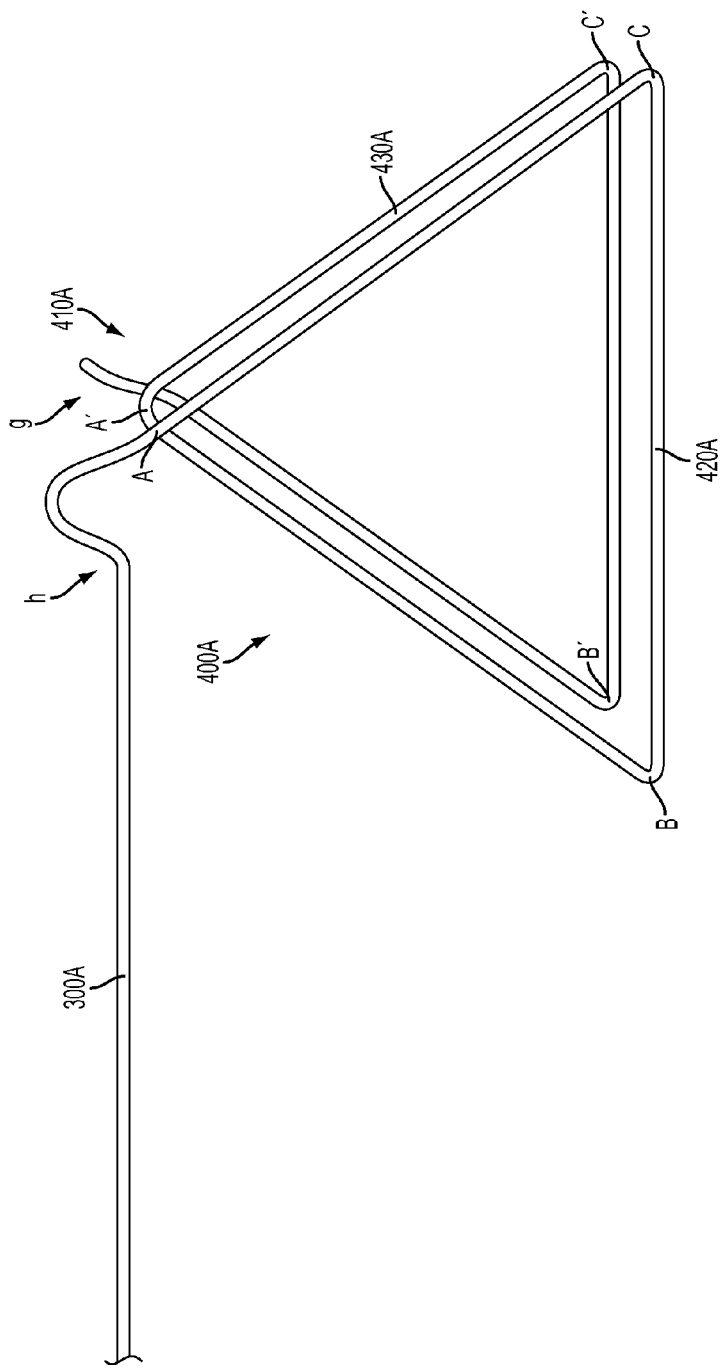

FIG. 2 is a top view of a cardiac pacing wire according to another embodiment.

Figure 3:
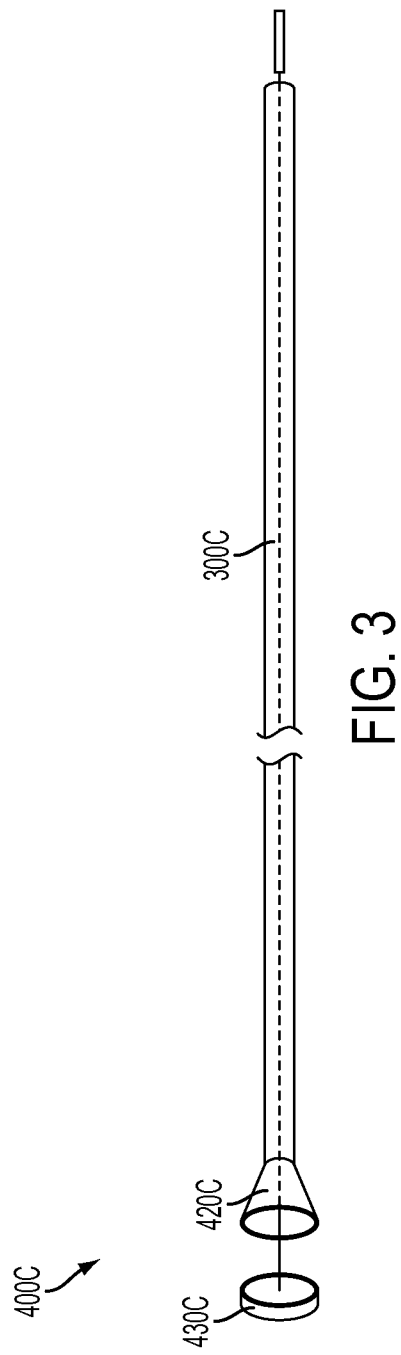

FIG. 3 is a schematic diagram of a pacing wire according to a further embodiment.

Figure 4:
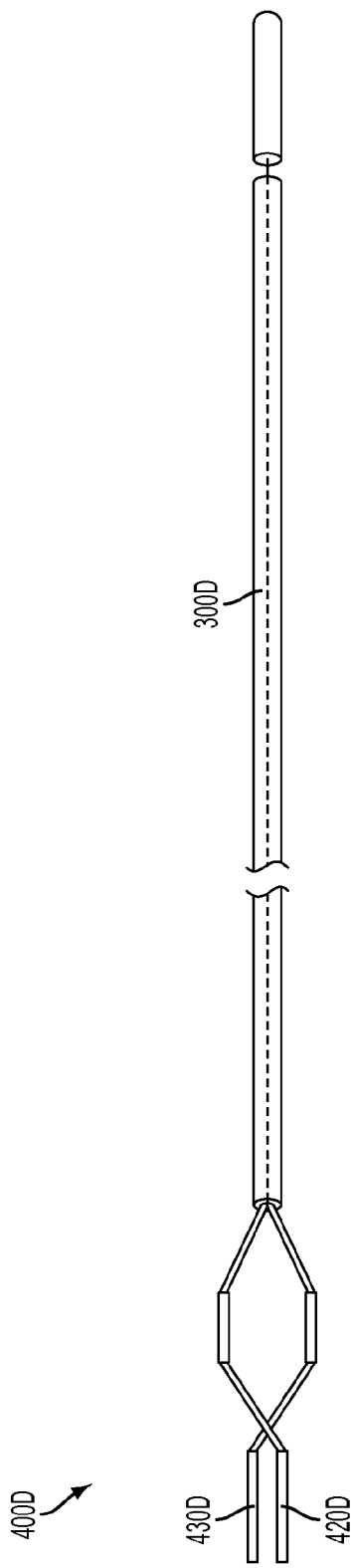

FIG. 4 is a schematic diagram of a pacing wire according to yet another embodiment.

Figure 5:
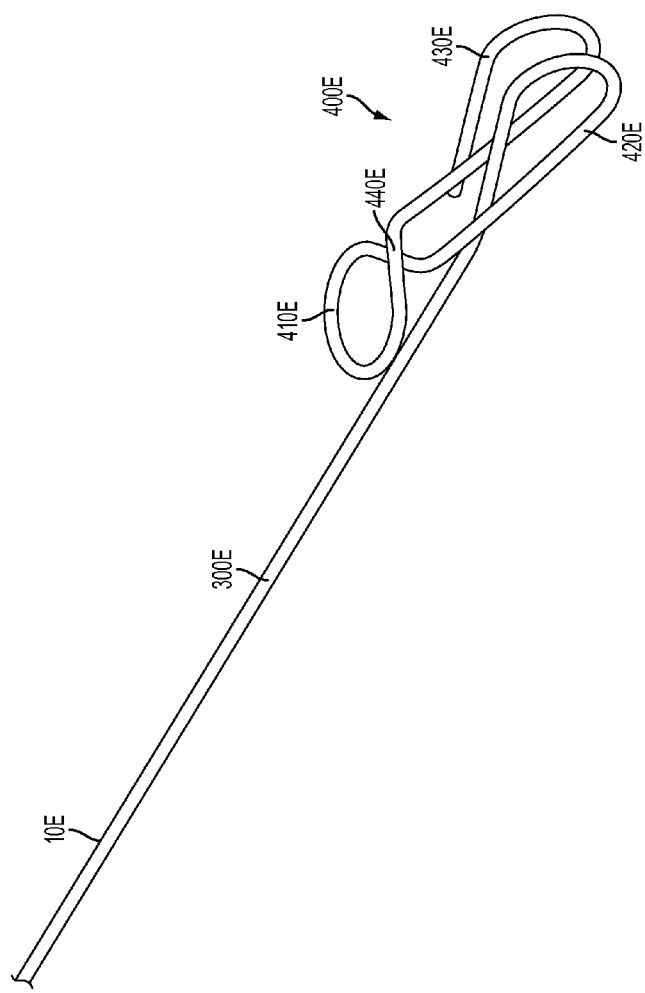

FIG. 5 is perspective view of a pacing wire according to a further embodiment.

Figure 6:
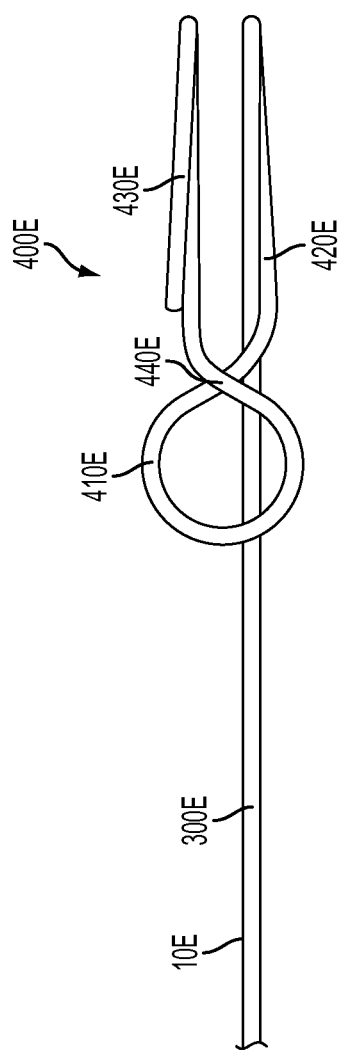

FIG. 6 is a top view of the pacing wire of FIG. 5 with the pacing wire's clamp in an open position.

Figure 7:
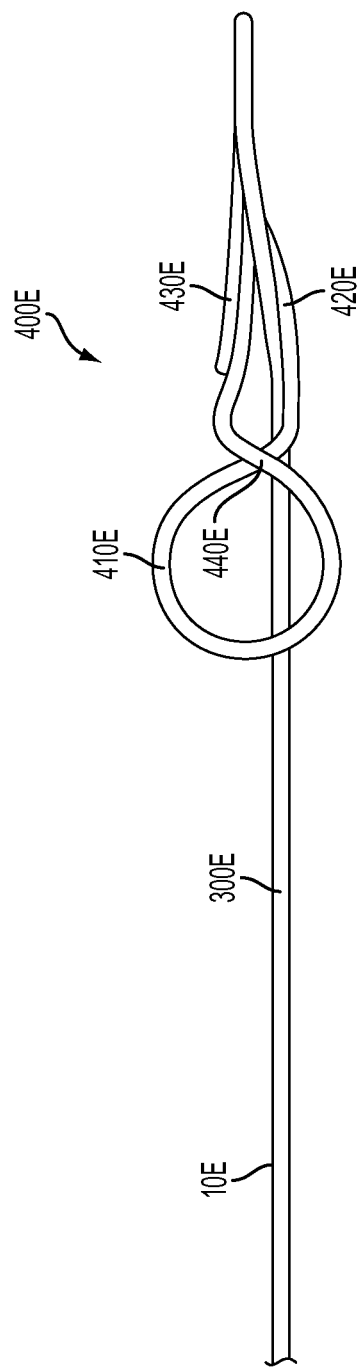

FIG. 7 is a top view of the pacing wire of FIG. 5 with the pacing wire's clamp in a closed position.

Figure 8:
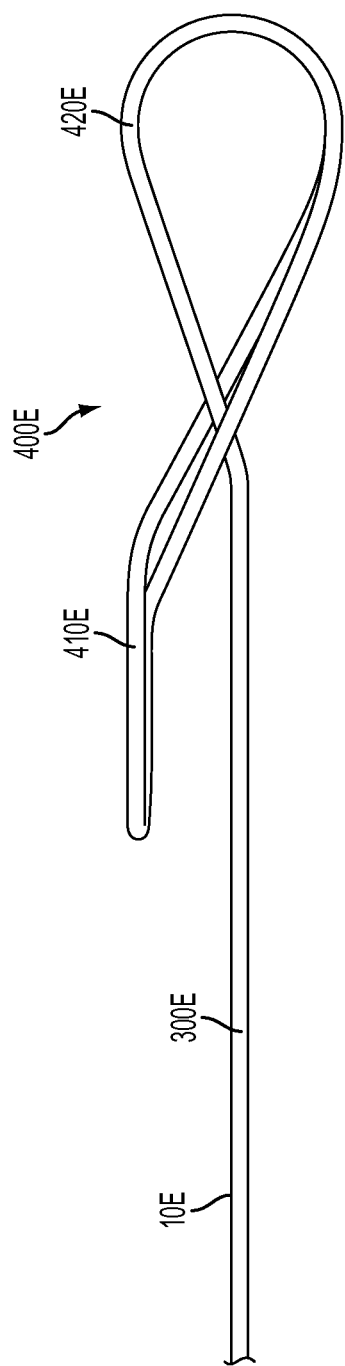

FIG. 8 is a side view of the pacing wire of FIG. 5 with the pacing wire's clamp in the open position.

Figure 9:
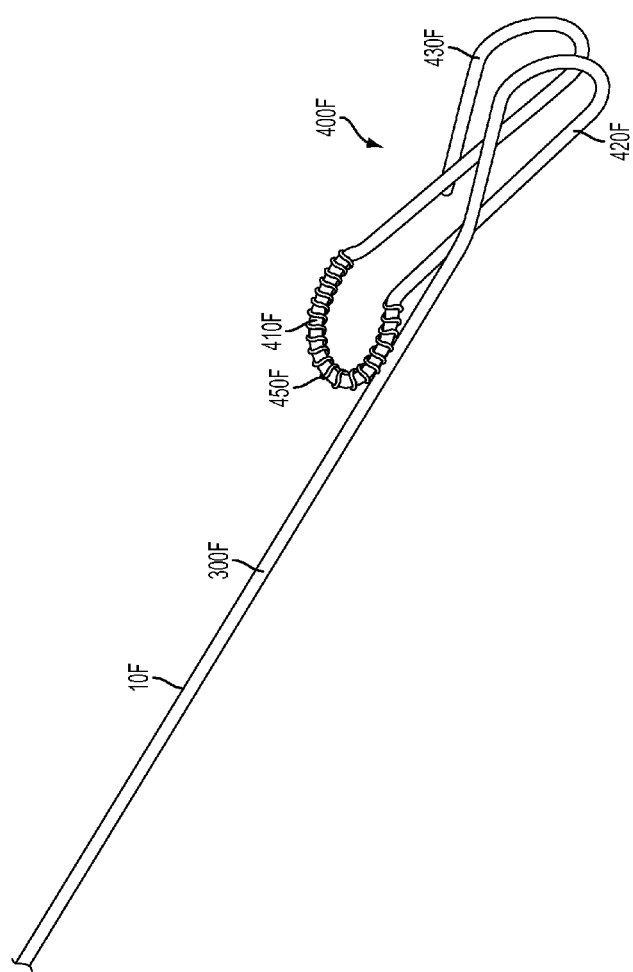

FIG. 9 is a perspective view of a pacing wire according to yet another embodiment.

Figure 10:
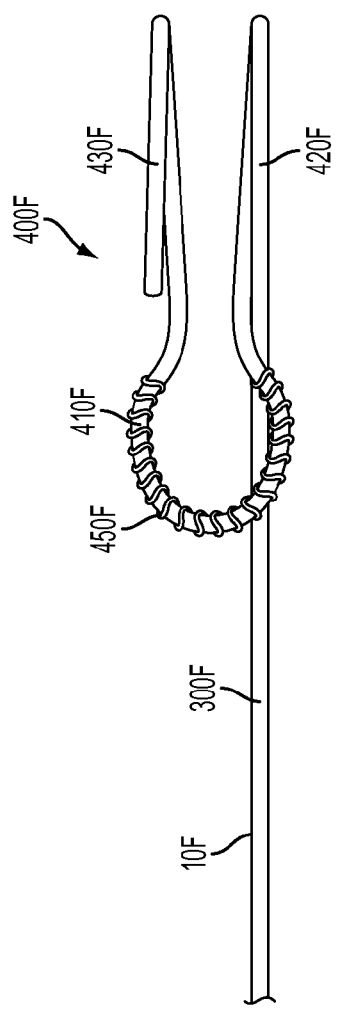

FIG. 10 is a top view of the pacing wire of FIG. 9 with a clamp in an open position.

Figure 11:
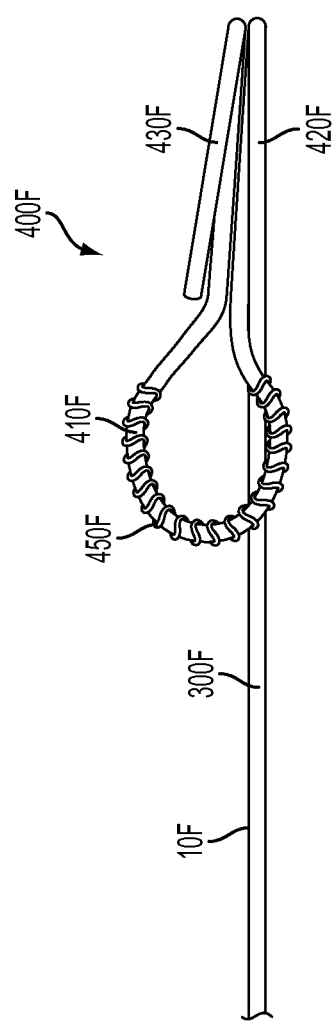

FIG. 11 is a top view of the pacing wire of FIG. 9 with the clamp in a closed position.

Figure 12:
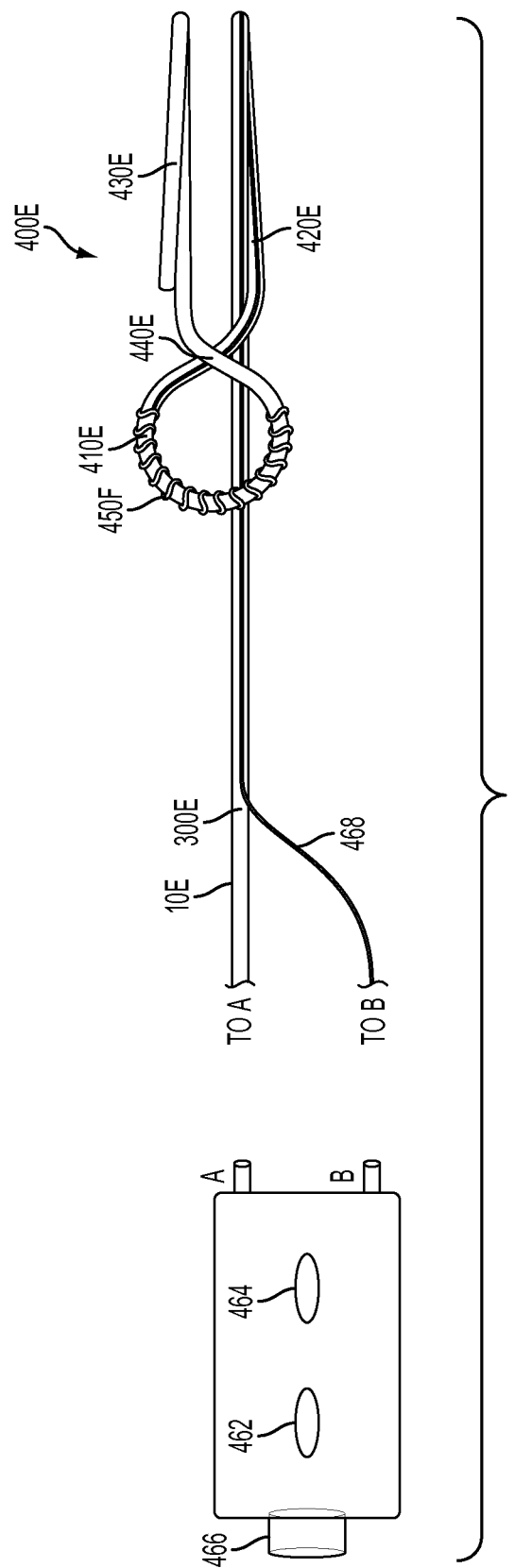

FIG. 12 is a side view of a pacing wire according to yet another embodiment.

DETAILED DESCRIPTION OF VARIOUS EMBODIMENTS

Various embodiments now will be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Various pacing wires described herein provide improvements over prior art pacing wires. Although, in various examples within this patent application, we refer to the heart as the primary organ being paced, it should be understood that the pacing wires described herein may be used to pace human or animal tissue other than the heart. For example, various embodiments may be used to pace a patient's central or peripheral nerves and/or the patient's brain. It should be understood that the clamp-shaped distal electrode (as described subsequently) can be configured to any other suitable shape to accommodate various surface areas of different organs.

A pacing wire 10 according to a particular embodiment is shown schematically in FIG. 1. In this embodiment, the pacing wire 10 includes an elongated flexible conductor 300 that may comprise, for example, a single filament conductor (or, alternatively, a multi-filament conductor) that is insulated except for its proximal end 200 and distal end 400 (which serve as electrodes). The pacing wire 10 further comprises a Keith needle 100 that is attached to the flexible conductor's proximal electrode 200 and that is scored for easy removal.

The flexible conductor's non-insulated distal end 400 comprises a wire (or other structure) that has been engineered and manufactured to assume a certain shape of a clamp as shown, for example, in FIG. 2. It should be understood that the flexible conductor's non-insulated distal end may be a continuous portion of the flexible conductor 300 or it may be separate wire (or other structure) that is suitably attached to the flexible conductor 300.

In the embodiment shown in FIG. 2, the clamp 400A (which may, for example, consist essentially of one or more shape metal alloys) is a single wire that is shaped to form two, substantially parallel, substantially planar, substantially triangular, clamp portions (e.g., first clamp portion A-B-C 420A and second clamp portion $A^1$-$B^1$-$C^1$ 430A) that are positioned adjacent a grip 410A that includes wire portions G and H.

In FIG. 2, the first clamp portion A-B-C 420A is in contact with the second clamp portion $A^1$-$B^1$-$C^1$ 430A and both of these wire loops are in an XY plane. Wire portions G and H are in a plane ZY that is substantially perpendicular to the XY plane. As a result, a user may selectively separate the clamp portion's respective distal edges (B-C and B1-C1) from each other by compressing wire portions G and H together (e.g., using a suitable clamp or a thumb and index finger).

Various portions of a pacing wire 10E according to an alternative embodiment are shown in FIG. 5. In this embodiment, the clamp 400E (which may, for example, consist of or consist essentially of one or more shape metal alloys) includes: (1) a substantially planar (e.g., planer), substantially tear-shaped (e.g., tear-shaped) first clamp portion 420E; (2) a substantially planar (e.g., planar), substantially tear-shaped (e.g., tear shaped) second clamp portion 430E that is substantially parallel (e.g., parallel) to the first clamp portion; and (3) a grip 410E that is substantially in the form of an oval. FIG. 7 shows the pacing wire 10E from FIG. 5 in a closed position, in which the first clamp portion 420E is in contact with the second clamp portion 430E and both clamp portions are in an XY plane. However, the grip 410E is in the XZ plane, which is substantially perpendicular to the XY plane. As a result, a user may selectively separate the clamp portion's respective distal edges from each other by compressing the grip 410E together (e.g., using a suitable mechanical device or a thumb and index finger).

In the embodiments shown in FIGS. 2, 5, and 6, a user may attach the pacing wire's clamp 400 to a portion of a patient's heart by squeezing the clamp's grip 410 which causes the clamp's opposing clamp portions 420, 430 (the clamp's "jaws") to open. The user then positions the clamp 400 so that a small piece of heart tissue is positioned between the clamp's opposing clamp portions 420, 430. The user then slowly releases the clamp 400 (which is mechanically biased to urge the opposing clamp portions 420, 430 towards each other), until the clamp 400 firmly grasps a small amount of the heart's tissue. In various embodiments, no holes are created in the heart which may minimize or entirely eliminate any bleeding associated with attaching the clamp 400 to the heart. In particular embodiments, the jaws of the clamp 400 are engineered to apply enough pressure to hold the tissue non-ischemically, yet firmly enough to prevent slippage.

By virtue of its design and material composition, in various embodiments, the clamp 400 can be applied and removed multiple times during an operation without injuring the heart or losing the clamp's grasping power. In particular embodiments, the proximal end of the pacing wire 10 sits outside the chest and allows a user to pace the heart if and when rhythm disturbances occur.

When it is time to remove the temporary pacing wire 10, the pacing wire's proximal electrode 200 can then be used to make the distal electrode 400 of the pacing wire, which is shaped as a clamp, change shape and configuration and become a loose, unshaped (e.g., substantially straight) wire. This releases the heart tissue from the clamp's grasp and preferably allows for an atraumatic disengagement of the clamp 400 and removal of the pacing wire 10 from the patient's chest.

As noted above, a user may selectively change the shape of the clamp 10 from a clamp configuration to a loose wire configuration by applying an energy source to the proximal end electrode 200 of the pacing wire 10, which sits outside the patient's chest. The energy source may for example, cause a change of the wire temperature of only a few degrees above or below what can be considered normal body temperature range. In particular embodiments, the temperature range (which may be any suitable temperature range) that makes the clamp-shaped wire assume a more natural straight wire configuration is determined, for example, by the composition of elements that constitute the SMA wire.

One suitable energy source would be one that causes a drop in temperature of the wire by a few degrees below normal body temperature. This can be achieved by safely immersing the proximal electrode of the wire in a cold material, such as liquid nitrogen, for few seconds causing transmittal of the cold from one end of the pacing wire (which is outside the patient's chest) to the other end of the wire, which is positioned within the patient's chest. After a predetermined contact time with the energy source (e.g., 10-20 seconds) cooling of the distal end 400 by a few degrees is achieved and the distal end wire 400 will denature, lose its grip on the heart, and become flexible enough to be removed at least substantially atraumatically from the patient's body.

Another example of a suitable energy source would be one that would heat the wire to a temperature that would be sufficient to cause the wire to change configuration. For example, bringing a heating filament into contact with the pacing wire's proximal electrode 200 for a short period time (e.g., 10-20 seconds) may cause sufficient heat to be transmitted to the clamp 400 to cause clamp 400 to denature, lose its grip on the heart, and become flexible enough to be removed at least substantially atraumatically from the patient's body. Yet another example of a suitable energy source that may heat the wire to a temperature sufficient to change its configuration may be introducing a voltage across the pacing wire.

As noted above, in further embodiments, other mechanical arrangements may be used to selectively disengage more traditional clamps that may, for example, not be made of materials that change form in response to changes in temperature. Two such embodiments are shown in FIGS. 8 and 9.

Combination Medical Pacing Wire Clamp

In various embodiments, it may desired for the pacing wire's clamp 400 to have two-way motion. In such embodiments, the clamp 400 may have two stable positions. In a first stable position, the clamp 400 may provide a substantially firm and safe connection to a tissue (e.g., a heart tissue). In a second stable position, the clamp 400 may be released from the tissue before a user removes the clamp 400 from a tissue and eventually from a patient's body with which the tissue is associated. This configuration involving at least two stable positions and two-way motion may be achieved by combining two shape memory alloy elements, two superelastic alloy elements, a mix of at least one superelastic alloy element and one shape memory alloy element, or any other suitable combination of materials. Each of the two elements may provide motion towards either an open or a closed position and may make the clamp 400 stable in one of the two stable positions. In particular embodiments, the superelastic element may provide a firm grabbing of the tissue. In various embodiments, the clamp may include a shape memory element that, when heated (for example through joule heating), may cause the superelastic element to disengage from the tissue. When heating is stopped, the clamp may resume its gripped configuration. In particular embodiments, the clamp 400 may be adapted to repeat the process of opening and closing the clamp 400 without substantially affecting the ability of the clamp 400 to grab and release tissue.

For cardiac pacing, a surgeon may put the pacing wire's clamp 400 on the tissue (e.g., the heart tissue). In various embodiments, the clamp may be removed and put back without any change in temperature. In particular embodiments, the superelasticity of the clamp 400 may make repeated deformations possible. At the time of removal of the pacing wire, a small current may be passed to the shape memory element of the clamp 400, which may cause slight heating, which in turn may release the clamp 400, leaving the lead wire free to be easily and safely removed from the patient's body.

In various embodiments of a medical pacing wire 10F, such as the embodiment shown in FIGS. 9-11, the pacing wire's clamp 400F may comprise two or more distinct pieces of material. In particular embodiments, a first piece may have a shape memory state that biases the clamp 400F toward a closed position as shown in FIG. 11. In various embodiments, a second piece may have a shape memory state that biases the clamp 400F toward an open position as shown in FIG. 10. In various embodiments, the pacing wire 10F may be adapted to produce conditions to place the first piece in its shape memory state and take the second piece out of its shape memory state in order to close the clamp 400F.

The pacing wire 10F may be further adapted to produce conditions to place the second piece in its shape memory state and take the first piece out of its shape memory state in order to open the clamp 400F. In various embodiments, these conditions may include, for example a change in temperature. In particular embodiments, the change in temperature may be a change from the typical temperature of an animal (e.g., a human) to a temperature above the typical temperature of an animal (e.g., a human). In various embodiments, the change in temperature may be a change to a temperature above about 37 degrees Celsius (e.g., the typical temperature of a human). In a particular embodiment, the temperature change may be a change to a temperature of between about 40 degrees Celsius and about 55 degrees Celsius.

In particular embodiments, the first piece may comprise a superelastic alloy that biases the clamp 400F toward the closed position. The second piece, which may be attached (e.g., to) the first piece may comprise a memory shape alloy that biases the clamp 400F toward the open position in response to being subjected to a change in temperature. An example of such an embodiment is described below.

Embodiments Including a Superelastic Piece that Biases the Clamp Towards the Closed Position In a particular embodiment of a medical pacing wire clamp 400, the first piece, which comprises (e.g., comprises, consists of, or consists essentially of) a superelastic alloy, may be in the shape of a clamp as shown in FIG. 5 or 9. As shown in FIG. 5, the clamp's distal end may include a scissored crossover 440E. Alternatively, as shown in FIG. 9, the clamp 400F may have a substantially U-shaped (e.g., U-shaped) distal end. In other embodiments, the clamp's distal end may be in any other suitable shape. In various embodiments, as shown in FIGS. 5 and 9, the clamp 400E, 400F may further comprise: (1) a substantially planar (e.g., planer), substantially tear-shaped (e.g., tear-shaped) first clamp portion 420E, 420F; and (2) a substantially planar (e.g., planar), substantially tear-shaped (e.g., tear shaped) second clamp portion 430E, 430F that is at least substantially parallel (e.g., parallel) to the first clamp portion. In other embodiments, the clamp 400 may include any other suitable clamp portions.

In the open position shown in FIG. 10, the first and second clamp portions 420F, 430F may be spaced apart a distance of between about 0.5 mm and about 3 mm. In a particular embodiment, when in the open position, the first and second clamp portions 420F, 430F may be spaced apart a distance of about 1 mm. In various embodiments, the distance between the clamp's distal end 410F and the first and second clamp portions' proximal ends may be between about 6 mm and about 17 mm. In a particular embodiment, the distance between the clamp's distal end 410F and the first and second clamp portions' proximal ends may be about 11 mm. In various embodiments, the clamp's distal end 410F may have a diameter that corresponds to the diameter of a circle whose diameter is between about 1.5 mm and about 5 mm.

As shown in FIGS. 9-11, the second piece 450F, which may, in various embodiments, comprise a memory shape alloy, is substantially helical (e.g., helical) and is disposed about a curved portion of the clamp's distal end 410F. In particular embodiments, the metal shape alloy (and any other metal shaped alloy described herein) may be a Nickel/Titanium alloy, a Copper/Zinc/Aluminum Alloy, a Copper/Aluminum/Nickel Alloy, or any other suitable memory shape alloy. In various embodiments, the inner radius of the substantially helical second piece 450F substantially corresponds to (e.g., corresponds to) the radius of the clamp's distal end 410F. As may be understood from FIG. 9, the clamp's distal end 400F extends through the second piece's substantially helical (e.g., helical) structure and the second piece 450F is wrapped a plurality of times around the clamp's distal end 410F. In the embodiment shown in this figure, the second piece 450F wraps around substantially all (e.g., all) of the clamp's substantially U-shaped distal end 410F. In other embodiments, the second piece 450F may wrap around any other suitable portion of the clamp's substantially U-shaped distal end 410F. In the embodiment shown in FIG. 9, the substantially helical second piece is substantially U-shaped (e.g., U-shaped) when in its memory state and when the clamp 400F is in the open position.

In particular embodiments, the second piece 450F is given a shape memory state of a substantially U-shaped (e.g., U-shaped) helix. In various embodiments, the second piece is adapted to return to its shape memory state position in response to a change in temperature (e.g., a change to a temperature above about 45 degrees Celsius or above about 50 degrees Celsius) or to any other suitable stimulus. Once the second piece 450F is given its shape memory state, it may be wrapped around the clamp's distal end 410F as described above. Once wrapped around the clamp's distal end 410F, the second piece 450F may be selectively used to bias the clamp 400F toward the open position (e.g., bias the first and second clamp portions 420F, 430F away from one another) by selectively increasing the temperature of the second piece 450F. In response to the change in temperature, the second piece 450F may bias the clamp 400F with at least a force sufficient to oppose the first piece's biasing of the clamp 400F toward the closed position.

In various embodiments, the pacing wire 10F may include a lead wire that runs along the length of the pacing wire and that is attached adjacent (e.g., to) the second piece 450F. The lead wire may be a conductive wire and may be adapted to transfer a voltage to the second piece 450F. This transfer of voltage may be configured to facilitate a change in temperature of the second piece 450F as described above. In a particular embodiment, a voltage of about 2 volts may be applied to the lead wire to facilitate the change in temperature in the second piece 450F that is suitable to move the second piece 450F from a non-memory state position into its memory state position. In other embodiments, other suitable voltages may be applied to facilitate the change in temperature. In particular embodiments, the voltage may be a voltage suitable to change the temperature in the second piece 450F to a temperature between about 45 degrees Celcius and about 55 degrees Celsius.

Embodiments Including a Superelastic Piece that Biases the Clamp Towards the Open Position In alternative embodiments, the first piece (e.g., the clamp 400F) may bias the clamp 400F toward the open position rather than the closed position. In such embodiments, the second piece 450F may selectively bias the clamp 400F toward the closed position in response to the second piece 450F being subjected to an appropriate stimulus (e.g., an appropriate change in temperature). A clamp with such components may be structurally similar to (e.g., the same as) the embodiment described above. In this alternative embodiment, the second piece 450F may respond to a change in temperature by biasing the clamp 400F toward (e.g., into) the closed position with at least a force sufficient to oppose the first piece's biasing of the clamp 400F toward the open position.

Embodiments Having a Scissored Distal End and a Superelastic Second Piece

In various embodiments, such as the embodiment shown in FIG. 12, the pacing wire clamp's distal end 410E includes a scissored crossover 440E in addition to a second piece 450F which, in various embodiments, comprises a memory shape alloy, is substantially helical (e.g., helical) and is disposed about a curved portion of the clamp's distal end 410E. In particular embodiments, the metal shape alloy (and any other metal shaped alloy described herein) may be a Nickel/Titanium alloy, a Copper/Zinc/Aluminum Alloy, a Copper/Aluminum/Nickel Alloy, or any other suitable memory shape alloy. In various embodiments, the inner radius of the substantially helical second piece 450F substantially corresponds to (e.g., corresponds to) the radius of the clamp's distal end 410E. As may be understood from FIG. 12, the clamp's distal end 400E extends through the second piece's substantially helical (e.g., helical) structure and the second piece 450F is wrapped a plurality of times around the clamp's scissored distal end 410E. In the embodiment shown in this figure, the second piece 450F wraps around substantially all (e.g., all) of the clamp's scissored distal end 410E. In other embodiments, the second piece 450F may wrap around any other suitable portion of the clamp's scissored distal end 410E. In the embodiment shown in FIG. 12, the substantially helical second piece is substantially U-shaped (e.g., U-shaped) when in its memory state and when the clamp 400E is in the open position.

In embodiments such as the embodiment shown in FIG. 12, the clamp 400E is substantially structurally similar to (e.g., structurally the same as) the clamp 400E in FIG. 5 described above and further comprises a second piece 450F that is substantially structurally similar to (e.g., structurally the same as) the second piece shown in FIG. 9 described above. In particular embodiments, the second piece 450F is given a shape memory state of a substantially U-shaped (e.g., U-shaped) helix. In various embodiments, the second piece is adapted to return to its shape memory state position in response to a change in temperature (e.g., a change to a temperature above about 45 degrees Celsius or above about 50 degrees Celsius) or to any other suitable stimulus.

Once the second piece 450F is given its shape memory state, it may be wrapped around the clamp's scissored distal end 410E as described above. Once wrapped around the clamp's distal end 410E, the second piece 450F may be selectively used to bias the clamp 400E toward the open position (e.g., bias the first and second clamp portions 420E, 430E away from one another) by selectively increasing the temperature of the second piece 450F. In response to the change in temperature, the second piece 450F may bias the clamp 400E with at least a force sufficient to oppose the first piece's biasing of the clamp 400E toward the closed position. As may be understood from FIG. 12, in various embodiments, the position of the clamp's scissored crossover 440E moves with respect to the clamp's distal end 410E when the clamp 400E is moved between the open and closed positions.

In various embodiments, such as the embodiment shown in FIG. 12, the pacing wire 10E includes a lead wire 468 that runs along the length of the pacing wire and that is attached adjacent (e.g., to) the second piece 450F. The lead wire may be a conductive wire and may be adapted to transfer a voltage to the second piece 450F. This transfer of voltage may be configured to facilitate a change in temperature of the second piece 450F as described above. In various embodiments, a battery 466 provides the voltage for facilitating the change in temperature of the second piece 450F.

Alternative Embodiments

Combination Medical Pacing Wire with Alternate Materials

In particular embodiments, the first piece of the pacing wire's clamp 400 may comprise a memory shape alloy, and the second piece may comprise a super elastic alloy. In certain embodiments, both pieces may be memory shape alloys. In various embodiments, the first and/or second piece may comprise any material suitable for maintaining a shape memory state.

Continuous Combination Medical Pacing Wire Clamp

In various embodiments, the clamp may comprise a substantially continuous (e.g., continuous) piece of material that combines at least a superelastic alloy and a memory shape alloy rather than two distinct pieces which separately contain each material.

Alternatively Shaped Second Piece

In various embodiments, the second piece may have a structure other than a substantially helical structure. In such embodiments, the second piece may comprise, for example, a linear spring, a torsion spring, or any other suitable structure. In particular embodiments, the second piece may be disposed on the clamp in a position other than that shown in FIGS. 9-11. In such embodiments, the second piece may be disposed in any suitable position for biasing the clamp in response to a suitable stimulus (e.g., a temperature change).

Open Clamp Indicator

In various embodiments, the pacing wire's clamp 400 may include a light that is configured to indicate when the clamp 400 is in the open position (e.g., and therefore safe to remove from a patient). In particular embodiments, the light may be adapted to turn on or off as the clamp is in the open or closed position respectively. In other embodiments, the light may be adapted to change colors in response to the clamp opening or closing. In other embodiments, the clamp may include any suitable indicator other than a light to indicate that the clamp is in the open or closed position.

FIG. 12 shows an embodiment of a pacing wire clamp 400E that includes indicators 462, 464 that are configured to show a user whether the pacing wire clamp 400E is in the open or closed position. As may be understood from this figure, the first indicator 464 may be a light, or any other suitable indicator, that is configured to illuminate when the pacing wire clamp 400E is in the open position. The second indicator 464 may be a light, or any other suitable indicator, that is configured to illuminate when the pacing wire clamp 400E is in the closed position. In various embodiments, the indicators 462, 464 may be different colors (e.g., the first indicator 462 may be green and the second indicator 464 may be red). In particular embodiments, the indicators 462, 464 are configured to change color at least partially in response to the change in temperature in the pacing wire (e.g., the change in voltage) described above.

CONCLUSION

Many modifications and other embodiments of the invention will come to mind to one skilled in the art to which this invention pertains having the benefit of the teachings presented in the foregoing descriptions and the associated drawings. For example, in various embodiments (including, potentially, certain embodiments described above), the pacing wire's clamp is made of a metal shape alloy (or other suitable material) that: (1) remains in the form of a clamp when the clamp is at a temperature that is within a temperature range that includes both typical operating-room temperatures and typical animal body temperatures; and (2) that relaxes into the form of a flexible wire in response to being cooled and/or heated outside of this range of temperatures. It should also be understood that the invention may take form in a variety of different mechanical and operational configurations. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

I claim:

1. A medical pacing wire comprising:
an elongated flexible conductor; and
a clamp comprising first and second opposing clamp members, said clamp being adapted to be moved between:
 (A) an open position in which said first and second clamp members are spaced a first distance apart from each other; and
 (B) a closed position in which said first and second clamp members are spaced a second distance apart from each other, said second distance being shorter than said first distance, wherein:
  said medical pacing wire comprises a memory shape alloy having a memory state;
  said clamp comprises a superelastic material;
  said medical pacing wire is adapted to allow a user to attach an electrode to a living tissue by:
   (A) moving said clamp into said open position;
   (B) positioning said clamp so that said living tissue is positioned between said clamp's first and second opposing clamp portions;
   (C) closing said clamp until said first and second clamp portions:
    (i) are in said closed position, and
    (ii) exert opposing compressive forces on opposite sides of said living tissue and thereby maintain said electrode in engagement with said living tissue; and
  said medical pacing wire is adapted so that causing said memory shape alloy to move from a non-memory state to a memory state causes said clamp to move from said closed position toward said open position;
  said memory shape alloy is in mechanical communication with said clamp so that causing said memory shape alloy to move from a non-memory state to a memory state causes said clamp to move from said closed position toward said open position;
  said medical pacing wire is adapted to allow a user to pace the living tissue by, while said clamp is maintaining said electrode in engagement with said living tissue, conveying an electrical current through said conductor, into said electrode, and into said living tissue;
  said medical pacing wire is adapted to allow a user to remotely cause said clamp to at least substantially release said living tissue;
  said clamp comprises a curved portion that is adapted to be moved between a first curved configuration and a second curved configuration, said second curved configuration being different from said first curved configuration;
  said clamp is configured so that moving said curved portion of said clamp from said first curved configuration into said second curved configuration causes said clamp to move from said closed position toward said open position;
  said memory shape alloy is wrapped a plurality of times around said curved portion of said clamp; and
  said memory shape alloy is adapted so that causing said memory shape alloy to move from said non-memory state to said memory state causes said curved portion of said clamp to move from said first curved configuration to said second curved configuration and to thereby move said clamp from said closed position toward said open position.

2. The medical pacing wire of claim 1, wherein said memory shape alloy is in the form of a wire that, when in its memory state, is substantially in the form of a helix.

3. The medical pacing wire of claim 1, wherein said curved portion comprises a scissored crossover.

4. A medical pacing wire comprising:
an elongated flexible conductor; and
a clamp comprising first and second opposing clamp members, said clamp being adapted to be moved between:
 (A) an open position in which said first and second clamp members are spaced a first distance apart from each other; and
 (B) a closed position in which said first and second clamp members are spaced a second distance apart from each other, said second distance being shorter than said first distance, wherein:
  said medical pacing wire comprises a memory shape alloy having a memory state;
  said clamp comprises a superelastic material;
  said medical pacing wire is adapted to allow a user to attach an electrode to a living tissue by:
   (D) moving said clamp into said open position;
   (E) positioning said clamp so that said living tissue is positioned between said clamp's first and second opposing clamp portions;
   (F) closing said clamp until said first and second clamp portions:
    (iii) are in said closed position, and
    (iv) exert opposing compressive forces on opposite sides of said living tissue and thereby maintain said electrode in engagement with said living tissue; and
  said medical pacing wire is adapted so that causing said memory shape alloy to move from a non-memory state to a memory state causes said clamp to move from said open position toward said closed position;

said memory shape alloy is in mechanical communication with said clamp so that causing said memory shape alloy to move from a non-memory state to a memory state causes said clamp to move from said open position toward said closed position;

said medical pacing wire is adapted to allow a user to pace the living tissue by, while said clamp is maintaining said electrode in engagement with said living tissue, conveying an electrical current through said conductor, into said electrode, and into said living tissue;

said medical pacing wire is adapted to allow a user to remotely cause said clamp to at least substantially release said living tissue;

said clamp comprises a curved portion that is adapted to be moved between a first curved configuration and a second curved configuration, said second curved configuration being different from said first curved configuration;

said clamp is configured so that moving said curved portion of said clamp from said first curved configuration to said second curved configuration causes said clamp to move from said open position toward said closed position;

said memory shape alloy is wrapped a plurality of times around said curved portion of said clamp;

said memory shape alloy is adapted so that causing said memory shape alloy to move from a non-memory state to a memory state causes said curved portion of said clamp to move from said first curved configuration to said second curved configuration and to thereby move said clamp from said open position toward said closed position.

5. The medical pacing wire of claim 4, wherein said memory shape alloy is in the form of a wire that, when in its memory state, is substantially in the form of a helix.

6. A medical pacing wire comprising:
an elongated flexible conductor; and
a clamp comprising first and second opposing clamp members, said clamp being adapted to be moved between:
(C) an open position in which said first and second clamp members are spaced a first distance apart from each other; and
(D) a closed position in which said first and second clamp members are spaced a second distance apart from each other, said second distance being shorter than said first distance, wherein:
said medical pacing wire is adapted to allow a user to attach an electrode to a living tissue by:
 (A) moving said clamp into said open position;
 (B) positioning said clamp so that said living tissue is positioned between said clamp's first and second opposing clamp portions;
 (C) closing said clamp until said first and second clamp portions:
  (i) are in said closed position, and
  (ii) exert opposing compressive forces on opposite sides of said living tissue and thereby maintain said electrode in engagement with said living tissue; and
said medical pacing wire is adapted to allow a user to pace the living tissue by, while said clamp is maintaining said electrode in engagement with said living tissue, conveying an electrical current through said conductor, into said electrode, and into said living tissue;

said medical pacing wire is adapted to allow a user to remotely cause said clamp to at least substantially release said living tissue; and said medical pacing wire further comprises an indicator, wherein said indicator is configured to indicate whether said clamp is in said open position.

7. A medical pacing wire comprising:
an elongated flexible conductor;
a superelastic clamp comprising first and second opposing clamp members, said clamp being adapted to be moved between:
(A) an open position in which said first and second clamp members are spaced a first distance apart from each other; and
(B) a closed position in which said first and second clamp members are spaced a second distance apart from each other, said second distance being shorter than said first distance, wherein, when said superelastic clamp is in its memory state, said superelastic clamp is in said closed position; and
a memory shape alloy that is attached in mechanical communication with said clamp so that causing said memory shape alloy to move from a non-memory state of said memory shape alloy to a memory state of said memory shape alloy causes said clamp to move from said closed position toward said open position, wherein:
said clamp comprises a curved portion that is adapted to be moved between a first curved configuration and a second curved configuration, said second curved configuration being different from said first curved configuration;
said clamp is configured so that moving said curved portion of said clamp from said first curved configuration to said second curved configuration causes said clamp to move from said closed position toward said open position;
said memory shape alloy is wrapped a plurality of times around said curved portion of said clamp; and
said memory shape alloy is adapted so that causing said memory shape alloy to move from said non-memory state to said memory state causes said curved portion of said clamp to move from said first curved configuration to said second curved configuration and to thereby move said clamp from said closed position toward said open position.

8. A medical pacing wire comprising:
an elongated flexible conductor;
a superelastic clamp comprising first and second opposing clamp members, said clamp being adapted to be moved between:
(A) an open position in which said first and second clamp members are spaced a first distance apart from each other; and
(B) a closed position in which said first and second clamp members are spaced a second distance apart from each other, said second distance being shorter than said first distance, wherein, when said superelastic clamp is in its memory state, said superelastic clamp is in said closed position; and
a memory shape alloy that is attached in mechanical communication with said clamp so that causing said memory shape alloy to move from a non-memory state of said memory shape alloy to a memory state of said memory shape alloy causes said clamp to move from said closed position toward said open position, wherein:
said clamp comprises a curved portion that is adapted to be moved between a first curved configuration and a second curved configuration, said second curved configuration being different from said first curved configuration;

said clamp is configured so that moving said curved portion of said clamp from said first curved configuration to said second curved configuration causes said clamp to move from said open position toward said closed position;

said memory shape alloy is wrapped a plurality of times around said curved portion of said clamp;

said memory shape alloy is adapted so that causing said memory shape alloy to move from a non-memory state to a memory state causes said curved portion of said clamp to move from said first curved configuration to said second curved configuration and to thereby move said clamp from said open position toward said closed position.

* * * * *

UNITED STATES PATENT AND TRADEMARK OFFICE
CERTIFICATE OF CORRECTION

PATENT NO. : 8,700,182 B2
APPLICATION NO. : 13/662949
DATED : April 15, 2014
INVENTOR(S) : Fady S. Wanna It is certified that error appears in the above-identified patent and that said Letters Patent is hereby corrected as shown below:

In the Claims

Column 12, Claim 4, Lines 53-63, should read:

(A) moving said clamp into said open position;
(B) positioning said clamp so that said living tissue is positioned between said clamp's first and second opposing clamp portions;
(C) closing said clamp until said first and second clamp portions:
(i) are in said closed position, and
(ii) exert opposing compressive forces on opposite sides of said living tissue and thereby maintain said electrode in engagement with said living tissue; and Column 13, Claim 6, Lines 42-48, should read:

(A) an open position in which said first and second clamp members are spaced a first distance apart from each other; and
(B) a closed position in which said first and second clamp members are spaced a second distance apart from each other, said second distance being shorter than said first distance, wherein:

Signed and Sealed this
Sixteenth Day of September, 2014

Michelle K. Lee
*Deputy Director of the United States Patent and Trademark Office*